US010052046B2

(12) United States Patent
Nickolas et al.

(10) Patent No.: US 10,052,046 B2
(45) Date of Patent: Aug. 21, 2018

(54) TROCHLEA-ANGLE MEASUREMENT TEMPLATE

(71) Applicant: ALLOSOURCE, Centennial, CO (US)

(72) Inventors: Brittany Nickolas, Highlands Ranch, CO (US); Christopher Mast, Denver, CO (US); Todd Huft, Highlands Ranch, CO (US); Meghan Gabriel, Denver, CO (US)

(73) Assignee: Allosource, Centennial, CO (US)

( * ) Notice: Subject to any disclaimer, the term of this patent is extended or adjusted under 35 U.S.C. 154(b) by 293 days.

(21) Appl. No.: 14/944,457

(22) Filed: Nov. 18, 2015

(65) Prior Publication Data

US 2016/0220149 A1 Aug. 4, 2016

Related U.S. Application Data

(60) Provisional application No. 62/110,991, filed on Feb. 2, 2015.

(51) Int. Cl.
| A61B 5/00 | (2006.01) |
| A61B 5/107 | (2006.01) |
| A61F 2/46 | (2006.01) |
| A61B 90/00 | (2016.01) |
| A61F 2/38 | (2006.01) |

(52) U.S. Cl.
CPC .......... *A61B 5/1071* (2013.01); *A61F 2/4657* (2013.01); *A61B 2090/067* (2016.02); *A61F 2/3877* (2013.01); *A61F 2002/4668* (2013.01)

(58) Field of Classification Search
CPC ..... A61B 5/107; A61B 5/1071; A61B 5/1077; A61F 2/4657; A61F 2002/4668
See application file for complete search history.

(56) References Cited

U.S. PATENT DOCUMENTS

| 4,097,999 A * | 7/1978 | Nowlin ..................... G01B 3/56 33/500 |
| 5,133,135 A * | 7/1992 | Durfee, Jr. .............. G01B 5/245 33/427 |
| 6,361,506 B1 * | 3/2002 | Saenger ............... A61B 5/1071 33/512 |
| 7,069,665 B1 * | 7/2006 | Adriano ................. A43B 7/142 33/3 R |

(Continued)

*Primary Examiner* — Max Hindenburg
(74) *Attorney, Agent, or Firm* — James A. Sheridan; Sheridan Law, LLC (57) ABSTRACT

The disclosure provides apparatus and methods of use pertaining to a measurement template for use in allograft preparation and processing. Specifically, the template may be used to measure the trochlea angle of the trochlea groove of the distal human femur. The measurement template may be formed of a flat metal plate having first and second ends, each forming a different angle designed to fit against the trochlea groove and provide an indication of the angle of the groove in relation to the angles formed by the template. The trochlea angle of the allograft may then be documented, allowing for proper matching between allograft tissue and transplant recipient physiology. The measurement template may be adapted for a variety of configurations depending on desired and/or common allograft requirements. Other embodiments are also disclosed.

14 Claims, 6 Drawing Sheets

(56) References Cited

U.S. PATENT DOCUMENTS

| | | | | |
|---|---|---|---|---|
| 7,172,562 | B2 * | 2/2007 | McKinley | A61B 5/103 |
| | | | | 33/511 |
| 7,458,977 | B2 * | 12/2008 | McGinley | A61B 17/15 |
| | | | | 600/426 |
| 8,864,689 | B2 * | 10/2014 | Pellis | A61B 5/1071 |
| | | | | 600/587 |
| 8,945,131 | B2 * | 2/2015 | Vanasse | A61B 5/1076 |
| | | | | 606/86 R |
| 9,050,049 | B2 * | 6/2015 | Ryan | A61B 5/1076 |
| 9,398,797 | B2 * | 7/2016 | Li | A45D 29/00 |
| 9,730,616 | B2 * | 8/2017 | Hershberger | A61B 5/1071 |

* cited by examiner

TROCHLEA-ANGLE MEASUREMENT TEMPLATE

REFERENCE TO PENDING PRIOR PATENT APPLICATION

This application claims the benefit under 35 U.S.C. 119 (e) of U.S. Provisional Patent Application No. 62/110,991, filed Feb. 2, 2015 by Brittany Nickolas, Christopher Mast, Todd Huft, and Meghan Gabriel for "TROCHLEA-ANGLE MEASUREMENT TEMPLATE," which patent application is hereby incorporated herein by reference.

BACKGROUND

An allograft includes bone or other tissues transplanted from one person to another. Allografts are used in a variety of medical treatments, such as knee replacements, bone grafts, spinal fusions, eye surgery, and skin grafts for the severely burned. Allografts come from voluntarily donated human tissue obtained from donor-derived, living-related, or living-unrelated donors.

Allograft processing centers are generally responsible for processing and cataloging allografts collected by organ procurement organizations ("OPOs"). The OPOs are, in turn, responsible for collecting and/or recovering voluntarily donated tissues and gathering any pertinent medical information about those tissues before transferring them to the processing center.

Once an allograft is received, the allograft processing center is then responsible for processing the allograft and readying it for safe and effective medical use. Such processing may involve several steps including inspection, testing, cleansing, and cataloging.

Figure 1:
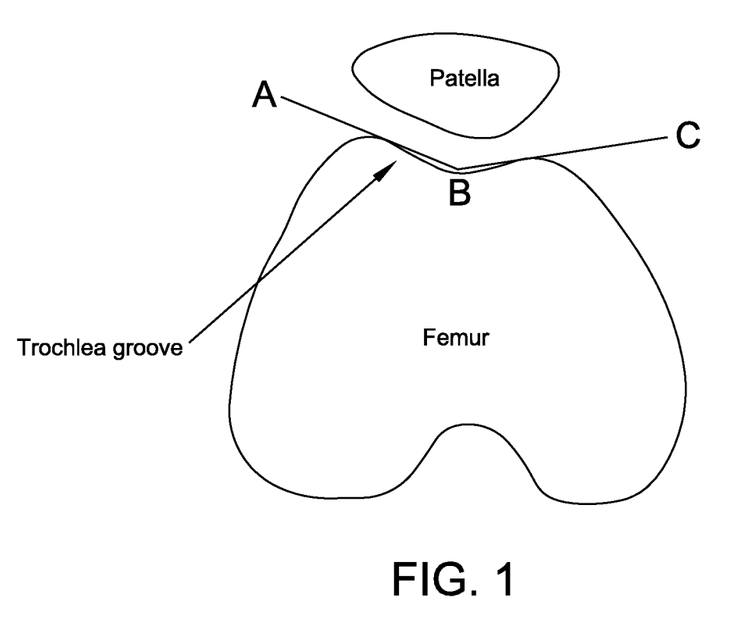
FIG. 1 illustrates a front plan view of the trochlea region of a human distal femur and mating Patella, specifically calling out the trochlea angle A-B-C.

When allografts involve the knee joint, processing centers are often called upon by surgeons performing the tissue transplants to provide allografts with specific physical characteristics pertaining to the trochlea region of the distal femur. Specifically, and as shown in FIG. 1, the Patella bone rides in the trochlea groove located in the trochlea region of the distal femur during normal movement of the knee joint. Because the trochlea groove varies in size and shape from person to person, proper matching between the trochlea groove and the Patella is required for proper movement of the knee joint upon a transplant involving allograft tissue of either the upper femur or the Patella. As a result, medical professionals such as allograft processing technicians, tissue bank technicians, and/or surgeons are often called upon to measure the trochlea or sulcus angle (hereinafter the "trochlea angle"), denoted by angle A-B-C in FIG. 1. This type of measurement may then be documented and cataloged during allograft production and processing, thereby allowing reliable, proper matching between the donor allograft and the receiving patient.

Currently, two primary measurement methods are used to measure the trochlea angle. Both techniques present significant accuracy, repeatability, and usability challenges. First, a preparing technician or other medical professional may measure the rise and run of the trochlea groove and mathematically calculate the trochlea angle. Depending on the shape of the trochlea groove, a correct rise-and-run measurement and subsequent angle calculation may require multiple measurements, coupled with time-consuming calculations that require additional instrumentation, such as a calculator, to be present during allograft processing.

A second existing measurement technique involves employing a straight edge and a protractor to directly measure the trochlea angle. This method requires more than one piece of equipment and, due to the mismatched shape of a protractor as compared to the three-dimensional trochlea groove, provides an unwieldy and often inaccurate measurement.

Both of these existing techniques introduce opportunities for human error into the measurement process and present sterilization challenges in that the required equipment cannot be easily sterilized after each use or reasonably purchased and stored in bulk such that individual items may be collected after a single use and sent out for sterilization at regular intervals. As a result, there is a need for an efficient, repeatable, and sterile method of measuring the trochlea angle during allograft preparation and on living patients undergoing a medical procedure.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

One embodiment provides a measurement template for measuring an angle of a trochlea groove of a distal human femur. The measurement template includes a handheld plate, where the handheld plate has a first end defining a first angle and a second end defining a second angle. The first angle may be sized to fit a first trochlea angle, and the second angle may be sized to fit a second trochlea angle.

Another embodiment provides a method of measuring a trochlea angle of a trochlea groove of a distal human femur using a measurement template. The measurement template may have a first end defining a first angle and a second end defining a second angle. The method may include (1) placing the first end of the measurement template within the trochlea groove; (2) determining whether the first end is larger than, equal to, or smaller than the trochlea groove; (3) upon determining that the first end is larger than the trochlea groove, recording the trochlea angle as an angle less than said first angle; and (4) upon determining that the first end is equal to or smaller than the trochlea groove: (a) placing the second end of the measurement template within the trochlea groove; (b) determining whether the second end is larger than, equal to, or smaller than the trochlea groove; (c) upon determining that the second end is larger than or equal to the trochlea groove, recording the trochlea angle as an angle between the first angle and the second angle; and (d) upon determining that the second end is smaller than the trochlea groove, recording the trochlea angle as an angle greater than the second angle. The method may further include steam sterilizing the measurement template after the recording of the trochlea angle as an angle less than the first angle, between the first and second angles, or greater than the second angle.

Yet another embodiment provides a method of measuring an angle of a trochlea groove of a distal human femur using a measurement template. The measurement template may include a first end forming a first angle and a second end forming a second angle. The method may include fitting the first end of the measurement template to the trochlea groove, comparing the first angle to the trochlea groove, and, based on the comparing of the first angle to the trochlea groove, determining the angle of the trochlea groove. The method may further include fitting the second end of the measurement template to the trochlea groove, comparing the second angle to the trochlea groove, and, based on the comparing of the second angle to the trochlea groove, refining the angle of the trochlea groove.

Other embodiments are also disclosed, and additional objects, advantages and novel features of the technology will be set forth in part in the following description, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

Various embodiments of the systems and methods described herein relate to a measurement template specifically adapted to measure the trochlea angle of donated allograft tissue or upon a living patient during a medical procedure. As discussed above, the trochlea angle is defined by the trochlea groove of the upper femur, shown by angle A-B-C of FIG. 1. The ability to quickly and accurately measure the trochlea angle with a simple, effective tool that may be steam sterilized along with other medical equipment allows allograft preparation technicians, tissue bank technicians, surgeons, and/or other medical personnel to more properly catalog allografts during allograft preparation and processing for proper matching between the donated tissue and the recipient patient.

Figure 2:
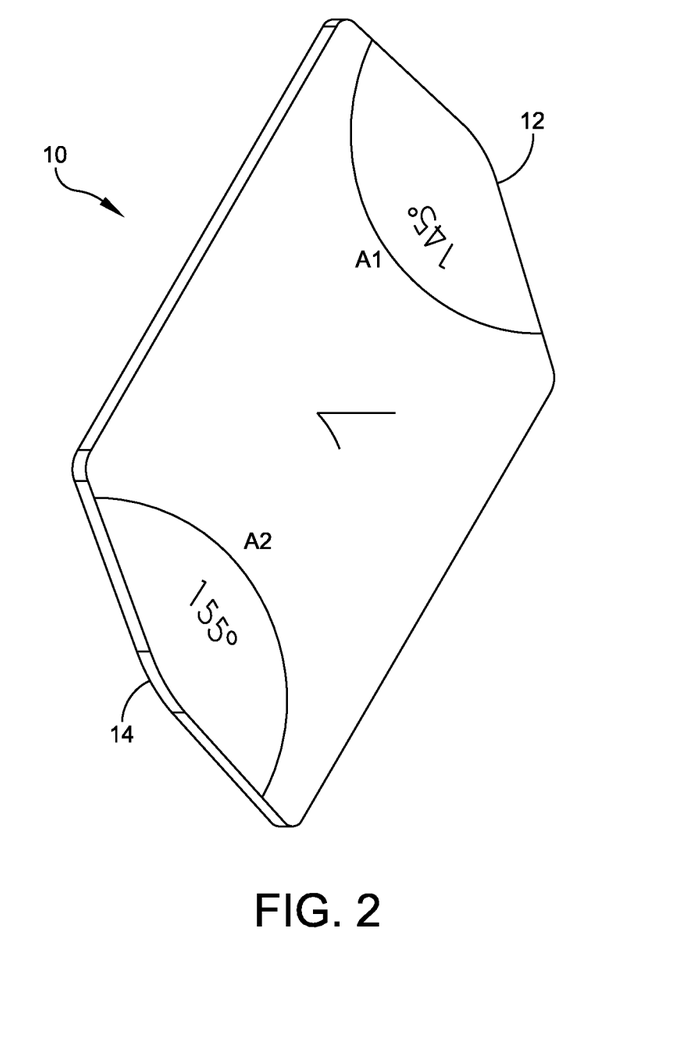
FIG. 2 provides a front prospective view of one embodiment of a trochlea-angle measurement template for use in measuring the trochlea angle A-B-C shown in FIG. 1.
Figure 3:
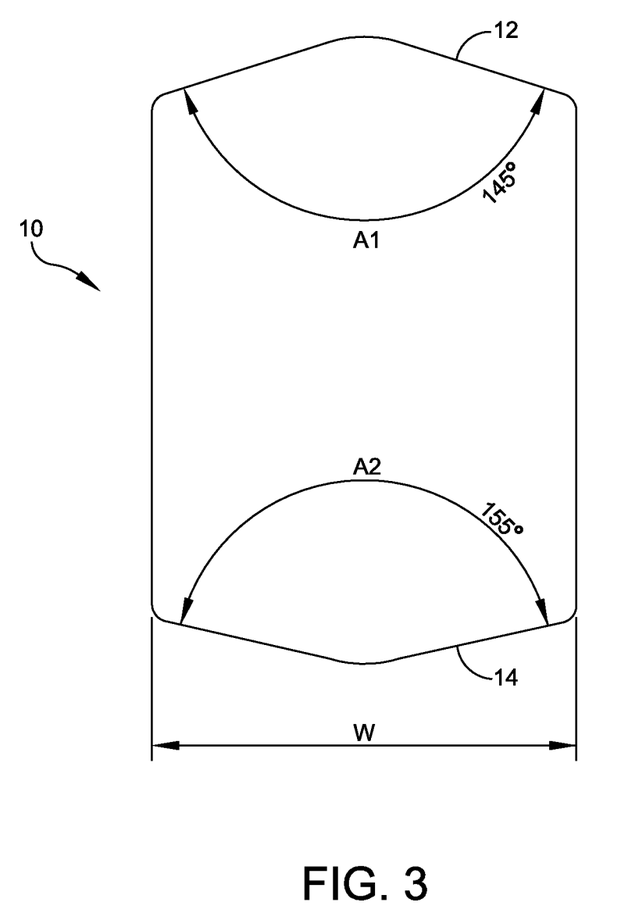
FIG. 3 provides a top plan view of the measurement template of FIG. 2.
Figure 4:
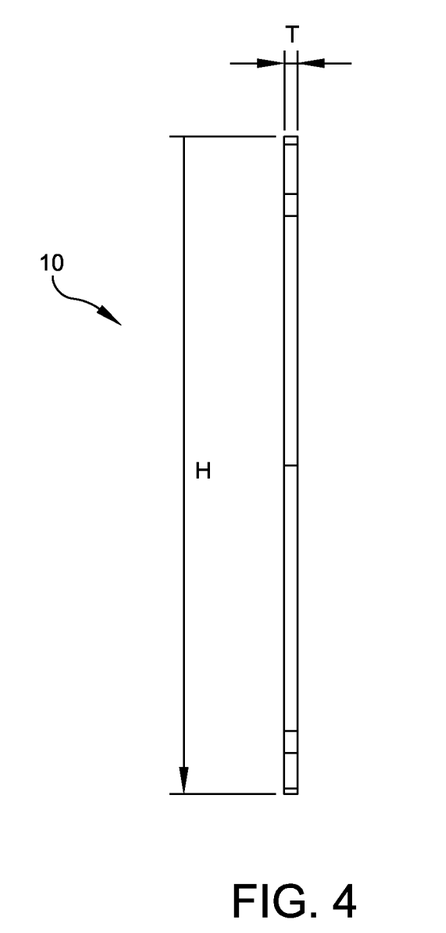
FIG. 4 provides a side plan view of the measurement template of FIG. 2.

FIGS. 2-4 illustrate front perspective, top, and side views of one embodiment of a trochlea-angle measurement template 10, respectively. In this embodiment, measurement template 10 has a first end 12 and a second end 14. In this embodiment, first end 12 may be pre-cut to form a first angle A1, while second end 14 may be pre-cut to form a second angle A2. In this embodiment, angle A1 may form a 145 degree angle and angle A2 may form a 155 degree angle. These angles span a common range for trochlea angles exhibited in men and women. As shown in FIGS. 2-3, the values for angles A1 and A2 may be visibly printed upon measurement template 10 to provide an easy guide for the user.

As shown in FIG. 3, measurement template 10 may have a defined width W. In one embodiment, width W may approximate 2 inches, or 5 cm, to account for the proper width of the trochlea region of the distal femur. In addition, and as shown in FIG. 4, embodiments of measurement template 10 may have a defined thickness T and height H. Thickness T may approximate 0.06 inches, or 0.15 cm, to accommodate a readily available gauge of stainless steel sheet (e.g., 16 gauge stainless steel sheet). Height H may approximate 2.89 inches, or 7.34 cm. While specific dimensions are described, it should be understood that template 10 may take any appropriate size, shape, and/or configuration to achieve its measurement purposes.

Template 10 may be formed of stainless steel (e.g., 316 stainless steel), lending the template rust and oxidation-resistant qualities and allowing template 10 to be a candidate for an efficient and effective post-use process of steam sterilization. After a singular use, template 10 may be steam sterilized on-site or, alternatively, stored with other medical equipment in specialized containers that are in queue for pick-up by an off-site sterilization service.

Figure 5:
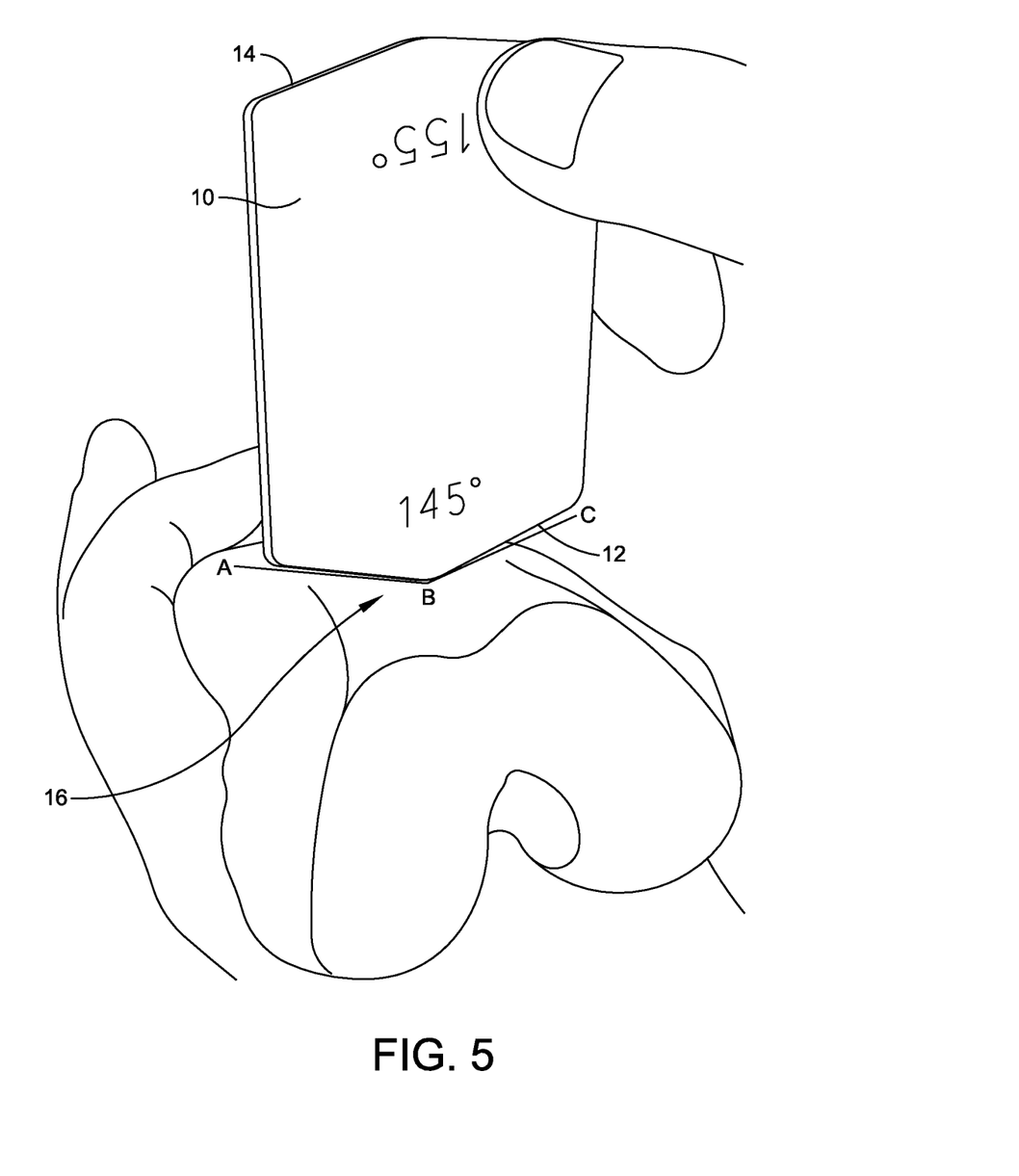
FIG. 5 provides a front perspective view of the measurement template of FIG. 2 as used to measure the trochlea angle A-B-C of a human femur.

To demonstrate the use of measurement template 10 during allograft production, FIG. 5 provides a perspective view of measurement template 10 as used to measure the trochlea angle A-B-C of a trochlea groove 16 of a distal femur. Specifically, FIG. 5 illustrates the placement of first end 12 of template 10 within trochlea groove 16.

Figure 6:
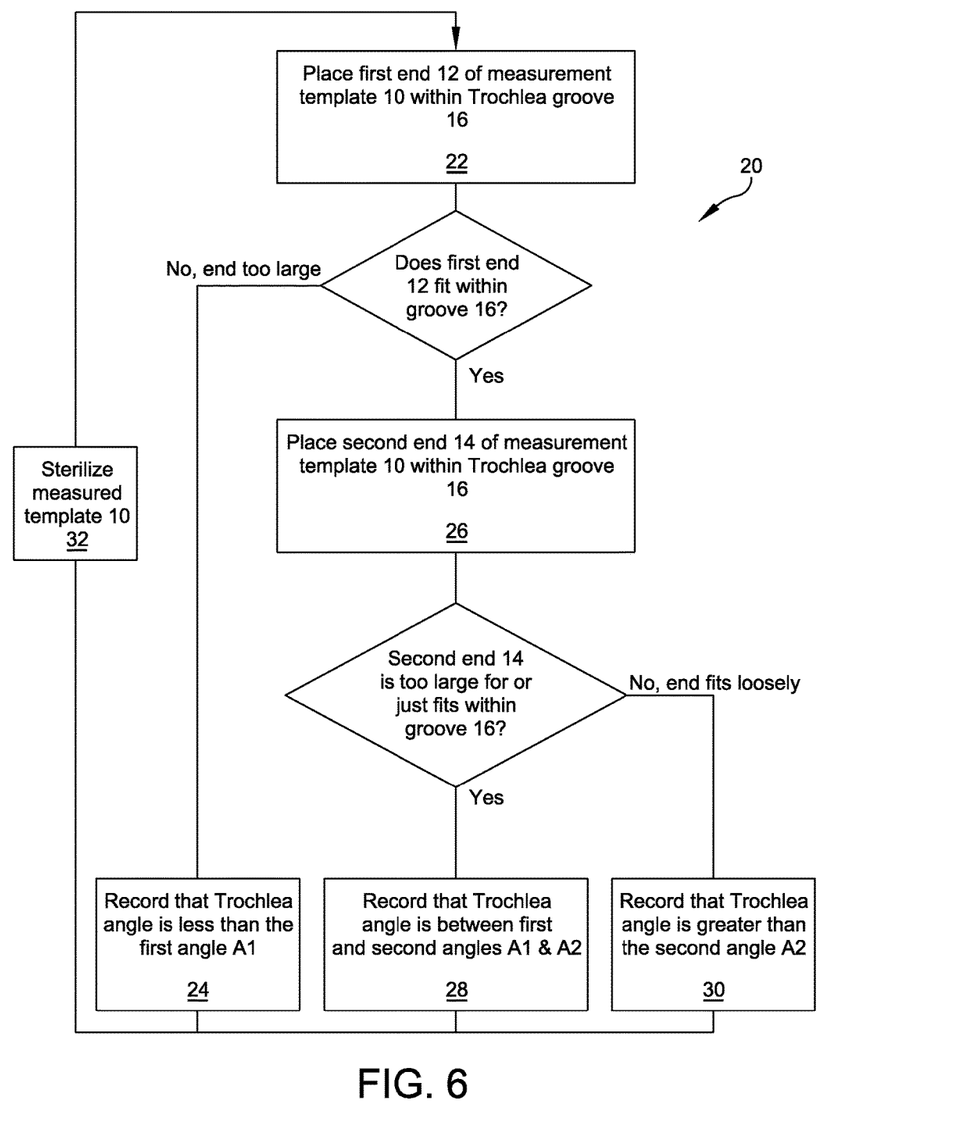
FIG. 6 provides a flow diagram depicting an exemplary method for measuring the trochlea angle of a human distal femur using the measurement template of FIG. 2.

FIG. 6 provides a flow diagram depicting an exemplary process 20 for measuring the trochlea angle using template 10. Process 20 initiates with the placement of first end 12 of template 10 within trochlea groove 16 (22), as detailed in FIG. 5. If first end 12 is too large such it does not fit within trochlea groove 16, then the preparing technician may record or document (24) that the trochlea angle is less than first angle A1, or, in the embodiment discussed in relation to FIGS. 2-5 above, less than 145 degrees.

If first end 12 fits within trochlea groove 16, the preparing technician may note that the trochlea angle of the allograft is equal to or greater than first angle A1 (e.g., 145 degrees) and flip template 10 before placing second end 14 within trochlea groove 16 (26) of the allograft. If second end 14 is too large or just fits within trochlea groove 16, the preparing technician may record (28) that the trochlea angle is between the first angle A1 and the second angle A2, or, in the embodiment discussed above, between 145 and 155 degrees. It should be understood that the term "between" is construed to include the referenced angles. If the second end 14 fits loosely within trochlea groove 16 of the allograft, the preparing technician may record (30) that the trochlea angle is greater than the second angle A2, or in the above-discussed embodiment, greater than 155 degrees. Once the measurement/recording is complete, measurement template 10 may be sterilized (32), either in house or it may be sent out for third-party sterilization along with other lab equipment/tools.

While the above-discussed embodiments of measurement template 10 and measuring process 20 are described in relation to specific first and second trochlea angles, namely 145 degrees and 155 degrees spaced 10 degrees apart, it should be noted that embodiments of measurement template 10 may be configured to measure any appropriate spread or resolution of angle measurement. Alternate embodiments may feature first and second ends cut at angles designed to measure finer or coarser resolutions. For instance, in other embodiments, the first and second ends of the measurement template could be cut to measure in 1, 5, and/or 20 degree increments, as appropriate or desired for the application. In one application, embodiments of measurement template 10 may be employed in consecutively smaller resolutions (e.g., beginning with a 10 degree delta between angles A1 and A2 and then progressively moving to smaller and smaller deltas), resulting in a refined trochlea-angle measurement that pinpoints a more exact trochlea angle.

By employing embodiments of the Sulcus or trochlea-angle measurement template 10, medical professionals have access to a fast, reliable, repeatable, and sanitary tool for accurately measuring the trochlea angle, thereby relieving them of more complicated measurement and/or calculation methods that require additional time and/or extraneous equipment that is either unsuited to the task or to the sanitized environment. Measurement template 10 provides an elegant and inexpensive solution that reaps numerous benefits over existing measurement methods.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A method of measuring a trochlea angle of a trochlea groove of a distal human femur using a measurement template having a first end defining a first angle and a second end defining a second angle, comprising:
    placing said first end of said measurement template within the trochlea groove;
    determining whether said first end is larger than, equal to, or smaller than the trochlea groove;
    upon determining that said first end is larger than the trochlea groove, recording the trochlea angle as an angle less than said first angle; and
    upon determining that said first end is equal to or smaller than said trochlea groove:
        placing said second end of said measurement template within said trochlea groove;
        determining whether said second end is larger than, equal to, or smaller than the trochlea groove;
        upon determining that said second end is larger than or equal to the trochlea groove, recording the trochlea angle as an angle between said first angle and said second angle; and
        upon determining that said second end is smaller than the trochlea groove, recording the trochlea angle as an angle greater than said second angle.

2. The method of claim 1, further comprising steam sterilizing said measurement template after said recording of the trochlea angle as an angle less than said first angle, between said first and second angles, or greater than said second angle.

3. The method of claim 1, wherein the trochlea groove is encompassed within an allograft.

4. The method of claim 1, wherein said first angle equals 145 degrees and said second angle equals 155 degrees.

5. The method of claim 1, wherein said second angle is ten degrees greater than said first angle.

6. The method of claim 1, wherein said second angle is 1 degree greater than said first angle.

7. The method of claim 1, wherein said handheld plate is formed of stainless steel.

8. A method of measuring an angle of a trochlea groove of a distal human femur using a measurement template having a first end forming a first angle and a second end forming a second angle, comprising:
    fitting said first end of said measurement template to the trochlea groove;
    comparing said first angle to the trochlea groove; and
    based on said comparing of said first angle to the trochlea groove, determining the angle of the trochlea groove;
    fitting said second end of said measurement template to the trochlea groove;
    comparing said second angle to the trochlea groove; and
    based on said comparing of said second angle to the trochlea groove, refining the angle of the trochlea groove.

9. The method of claim 8, further comprising sterilizing said measurement template after said refining said angle of the trochlea groove.

10. The method of claim 8, wherein said measurement template is formed of stainless steel.

11. The method of claim 8, wherein said second angle exceeds said first angle.

12. The method of claim 11, wherein said second angle equals 155 degrees and said first angle equals 145 degrees.

13. The method of claim 11, wherein said second angle exceeds said first angle by 10 degrees.

14. The method of claim 11, wherein said second angle exceeds said first angle by 1 degree.

* * * * *